(12) United States Patent
Gardner et al.

(10) Patent No.: US 9,514,360 B2
(45) Date of Patent: Dec. 6, 2016

(54) MANAGEMENT OF REFERENCE SPECTRAL INFORMATION AND SEARCHING

(75) Inventors: Craig M. Gardner, Belmont, MA (US); Robert L. Green, Haverhill, MA (US)

(73) Assignee: Thermo Scientific Portable Analytical Instruments Inc., Tewksbury, MA (US)

( * ) Notice: Subject to any disclaimer, the term of this patent is extended or adjusted under 35 U.S.C. 154(b) by 1076 days.

(21) Appl. No.: 13/363,171

(22) Filed: Jan. 31, 2012

(65) Prior Publication Data

US 2013/0197815 A1  Aug. 1, 2013

(51) Int. Cl.
  G06K 9/62 (2006.01)
  G06F 19/24 (2011.01)
  G06K 9/00 (2006.01)
  G06K 9/38 (2006.01)

(52) U.S. Cl.
  CPC ............ G06K 9/00543 (2013.01); G06K 9/38 (2013.01); G06K 9/6212 (2013.01); G06K 9/6215 (2013.01); *G06F 19/24* (2013.01)

(58) Field of Classification Search
  CPC ........................... G06F 19/24; G06K 9/00543
  See application file for complete search history.

(56) References Cited

U.S. PATENT DOCUMENTS

| | | | |
|---|---|---|---|
| 7,555,393 B2 | 6/2009 | Sadygov et al. | |
| 7,595,484 B2 | 9/2009 | Yokosuka et al. | |
| 2003/0200244 A1 | 10/2003 | Abraham et al. | |
| 2003/0219715 A1* | 11/2003 | Lam et al. | 435/4 |
| 2004/0195500 A1* | 10/2004 | Sachs et al. | 250/282 |
| 2007/0282537 A1 | 12/2007 | Freitas et al. | |

FOREIGN PATENT DOCUMENTS

| | | |
|---|---|---|
| RU | 2389983 C2 | 5/2010 |
| WO | 2005003308 A2 | 1/2005 |
| WO | WO2005003308 A2 | 1/2005 |

OTHER PUBLICATIONS

Veltri, Pierangelo, "Algorithms and tools for analysis and management of mass spectrometry data", Briefings in Bioinformatics, vol. 9, No. 2, 2008, pp. 144-155.

Yen, et al., "Spectrum-to-Spectrum Searching Using a Proteome-wide Spectral Library", Molecular & Cellular Proteomics, vol. 10, No. 7, Apr. 30, 2011, pp. 1-15.

Sadygov, et al., "A Hypergeometric Probability Model for Protein Identification and Validation Using Tandem Mass Spectral Data and Protein Sequence Databases", vol. 75, No. 15, Aug. 1, 2003, pp. 3792-3798.

(Continued)

*Primary Examiner* — Janet Suglo
(74) *Attorney, Agent, or Firm* — William R. McCarthy, III

(57) ABSTRACT

A processing application receives peak information associated with multiple known references samples. The processing application partitions a spectrum into multiple different sized range bins such that a substantially equal number of the peaks associated with the known reference samples reside into each of the multiple different sized range bins. To identify a set of candidate reference samples in a library of reference samples that potentially are a good match an unknown sample under test, the processing application compares peaks associated with the unknown sample to the multiple different sized range bins. The greater the number of range bin matches based on peaks in the unknown sample and peaks in a corresponding reference sample, the greater the likelihood that the unknown sample matches the corresponding reference sample.

26 Claims, 14 Drawing Sheets

(56) References Cited

OTHER PUBLICATIONS

Tabb, et al., "MyriMatch: Highly Accurate Tandem Mass Spectral Peptide Identification by Multivariate Hypergeometric Analysis", Journal of Proteome Research, vol. 6, No. 2, Jan. 18, 2007, pp. 654-661.

Sadygov, et al., "A New Probabilistic Database Search Algorithm for ETD Spectra", Journal of Proteome Research, vol. 8, No. 6, Jun. 5, 2009, pp. 3198-3205.

International Search Report, PCT/US2013/021847, Apr. 17, 2013, p. 3.

Clerc, J.T., et al., "Performance Analysis of Infrared Library Search Systems", Mikrochim. Acta (Wien), 1986 II, 217-242.

Zurcher, M., et al., "General Theory for Similarity Measures for Library Search Systems", Anal. Chim. Acta, 206 (1988) 161-172.

Sadygov, Rovshan G., et al., "A Hypergeometric Probability Model for Protein Identification and Validation Using Tandem Mass Spectral Data and Protein Sequence Databases", Analystical Chemistry, vol. 75., No. 15, Aug. 1, 2003, 3792-3798.

\* cited by examiner

| NO. OF PEAKS | KNOWN SAMPLE | BIN 210-1 | BIN 210-2 | BIN 210-3 | BIN 210-4 | BIN 210-5 | BIN 210-6 | BIN 210-7 | BIN 210-8 | BIN 210-9 | BIN 210-10 |
|---|---|---|---|---|---|---|---|---|---|---|---|
| (6) | REF. A | PA1 | PA2 | | | PA3 | PA4 | PA5 | | | PA6 |
| (3) | REF. B | | | | PB1 | | | | PB2 | PB3 | |
| (5) | REF. C | PC1 | | | PC2 | | PC3 | | PC4 | | PC5 |
| (3) | REF. D | PD1 | PD2 | | | | | | | | PD3 |
| (4) | REF. E | | | | PE1 | PE2 PE3 | | | PE4 | | |
| (5) | REF. F | | PF1 | | | | PF2 | PF3 | PF4 | PF5 | |
| (5) | REF. G | | | PG1 PG2 | PG3 | | | PG4 | | PG5 | |
| (3) | REF. H | PH1 | | PH2 | | | | | | PH3 | |
| (6) | REF. K | | PK1 | PK2 | | PK3 | PK4 | PK5 | | PK6 | |

| | BINARY STRING 510 OF UNKNOWN SAMPLE | 1 SP1 → | 1 SP2 → | 0 | 0 | 0 | 1 SP3 → | 0 | 0 | 0 | 1 SP3 → | |
|---|---|---|---|---|---|---|---|---|---|---|---|---|
| CANDIDATE | KNOWN SAMPLE | BIN 210-1 | BIN 210-2 | BIN 210-3 | BIN 210-4 | BIN 210-5 | BIN 210-6 | BIN 210-7 | BIN 210-8 | BIN 210-9 | BIN 210-10 | |
| YES | REF. A | PA1 | PA2 | | | PA3 | PA4 | PA5 | | | PA6 | |
| NO | REF. B | | | | PB1 | | | | PB2 | PB3 | | |
| YES | REF. C | PC1 | | | PC2 | | PC3 | | PC4 | | PC5 | |
| YES | REF. D | PD1 | PD2 | | | | | | | | PD3 | |
| NO | REF. E | | | | PE1 | PE2 PE3 | | | PE4 | | | |
| YES | REF. F | | PF1 | | | | PF2 | PF3 | PF4 | | PF5 | |
| NO | REF. G | | | PG1 PG2 | PG3 | | | PG4 | | PG5 | | |
| YES | REF. H | PH1 | | PH2 | | | | | | PH3 | | |
| YES | REF. K | | PK1 | PK2 | | PK3 | PK4 | PK5 | | PK6 | | |

| UNKNOWN SAMPLE | | 1 | 1 | 0 | 0 | 0 | 1 | 0 | 0 | 0 | 1 | |
|---|---|---|---|---|---|---|---|---|---|---|---|---|
| | | SP1→ | SP2→ | | | | SP3→ | | | | SP4→ | |
| CANDIDATE SAMPLE | | BIN 110-1 | BIN 110-2 | BIN 110-3 | BIN 110-4 | BIN 110-5 | BIN 110-6 | BIN 110-7 | BIN 110-8 | BIN 110-9 | BIN 110-10 | BINARY STRING |
| REF. A | | 1 | 1 | 0 | 0 | 1 | 1 | 1 | 0 | 0 | 1 | 610-1 |
| REF. C | | 1 | 0 | 0 | 1 | 0 | 1 | 0 | 1 | 0 | 1 | 610-2 |
| REF. D | | 1 | 1 | 0 | 0 | 0 | 0 | 0 | 0 | 0 | 1 | 610-3 |
| REF. F | | 0 | 0 | 1 | 0 | 0 | 0 | 0 | 1 | 0 | 1 | 610-4 |
| REF. H | | 1 | 1 | 1 | 0 | 1 | 1 | 1 | 0 | 0 | 1 | 610-5 |
| REF. K | | 0 | 1 | 1 | 0 | 1 | 0 | 1 | 0 | 1 | 0 | 610-6 |

600

| CANDIDATE SAMPLE | k MATCHES | N BINS | n PEAKS IN UNKNOWN | m PEAKS IN REF | P-VALUE OR (1-CDF) |
|---|---|---|---|---|---|
| REF. A | 4 | 10 | 4 | 6 | 0.0000 |
| REF. C | 3 | 10 | 4 | 5 | 0.2381 |
| REF. D | 3 | 10 | 4 | 3 | 0.0000 |
| REF. F | 3 | 10 | 4 | 5 | 0.2381 |
| REF. H | 1 | 10 | 4 | 3 | 0.3333 |
| REF. K | 2 | 10 | 4 | 6 | 0.4524 |

FIG. 7

MANAGEMENT OF REFERENCE SPECTRAL INFORMATION AND SEARCHING

BACKGROUND

It is known that a spectral analysis can be performed on a sample to identify its type. For example, a spectral analysis of an unknown sample under test can include identifying one or more peak wavelength values. Careful matching of the peak wavelengths of the unknown sample to a peak signature of a known reference sample can indicate whether the unknown sample is likely the same matter as the reference sample.

In modern multi-channel instrumentation, a reference database in which to search and match an unknown sample to a known sample can require a substantial amount of processing and storage resources. For example, it is not uncommon to receive a spectral analysis including a continuum of a thousand or more data points for each measurement of an unknown sample.

Furthermore, in conventional spectrum searching applications, it is not uncommon that a reference database includes more than 10,000 sets of spectral information; one set of spectral information for each reference sample.

Each set of spectral information for a respective reference sample can consist of a thousand or more data points defining peaks, valleys, etc. Matching of spectral information (e.g., a thousand or more data points) in an unknown sample to a corresponding one of more than 10,000 sets of spectral information (e.g., a thousand or more data points) may be computationally challenging. For example, when a 2000 point unknown spectrum is searched against a library of 10,000 reference spectra (each of which contain 2000 channels of information), 20,000,000 or more operations (point by point comparisons) must be executed if no provisions are taken to use a computationally efficient search methodology.

One approach to make the search methodology more efficient is to compress the spectral data into a binary format prior to analysis. In accordance with conventional spectroscopy, one prior approach to binarize a spectrum is to make an assessment regarding the presence or absence of a peak. When comparing two spectra, such as spectrum A and spectrum B, one approach would be to look at a table of peaks for spectrum A and assign a value of one to any location where spectrum B also contains a feature within n wavenumbers (or other suitable units, e.g. pixels, m/z, etc.) of that peak. A value of zero is assigned to any location of the peaktable for spectrum A where spectrum B does not contain a peak. This approach was described by Clerc, et al., in the 1980s.

Although this conventional approach provides a general similarity ranking, it does not afford any kind of probabilistic interpretation. Also worth noting (and noted by Clerc) is that, in accordance with this conventional approach, the scores of candidate matches depend on the direction of the search (results are non-symmetric). For example suppose spectrum A contains 10 peaks, spectrum B contains 12 peaks, and 8 of the peaks are found to be in common. Since respective scores are normalized based on the number of peaks present, values of 8/10 or 8/12 can be generated.

BRIEF DESCRIPTION OF EMBODIMENTS

As discussed above, conventional techniques of matching an unknown sample to a known reference sample in a database based on a spectral analysis can be challenging due to the amount of data points that must be compared to accurately identify a proper match. In many cases, it is undesirable to require lengthy computations to determine one or more references that match an unknown sample to identify its type.

Moreover, conventional spectral matching techniques are typically inadequate to quickly identify matches because such techniques only provide a listing indicating which of multiple possible references matches the unknown sample. The conventional ordered list of candidates can be misleading. For example, in accordance with conventional lists, it is not known whether a first candidate reference sample (i.e., first known sample) in a list is any more likely as being a match to the sample under test than a second candidate reference sample (i.e., second known sample) in the list. In other words, conventional techniques typically do not provide any useful probability information indicating which of multiple candidates in a list is more likely to be a proper match to an unknown sample under test.

In contrast to conventional techniques, in general, embodiments herein include conversion of spectral processing information associated with one or more reference samples into a more compact form. Additionally, embodiments herein include a computationally efficient methodology of searching a spectral library. For example, based at least in part on a unique way of managing information in a spectral library (e.g., compressing data), fewer mathematical operations are necessary to perform spectral searching to identify a manageable subset of reference samples that are more likely to match the unknown sample. Note that the processing as discussed herein is well suited for use in any type of spectroscopy applications in which spectral peaks provide clues as to an identity of an unknown sample under test.

More specifically, according to one embodiment, a processing application receives information specifying a corresponding set of peaks for each reference sample of multiple references samples in a library. The processing application (e.g., spectral data processor) partitions a spectrum to include multiple bins of different width, referred to in the remainder of this document as range bins. The spectrum can be partitioned such that each of the peaks in the multiple reference samples resides in one or more of the multiple different sized range bins.

In one embodiment, partitioning of the spectrum into multiple different sized range bins includes defining widths and/or boundaries of each of the multiple different sized range bins such that a substantially equal number of the peaks associated with the reference samples fall into each of the multiple different sized range bins. To identify candidate reference matches, in general, the processing application compares, maps, indexes, etc., peaks associated with an unknown sample to the multiple different sized range bins. Matching of peaks in the unknown sample under test to one or more of the range bins enables an analyzer to identify reference samples that are candidates for being a good match to the unknown sample under test. In other words, the greater the number of common range bins shared between the unknown sample under test and a respective reference sample, the more likely the unknown sample under test matches the respective reference sample.

In accordance with one embodiment, note that the techniques as discussed herein can include an analysis and/or comparison of an unknown sample to all possible reference samples in a pool. For each of one or more reference samples in the pool, embodiments herein can further include generating a corresponding p-value (e.g., probability information) for each of any or all of the reference samples. As discussed herein, further analysis of the probability information enables identification of good or best possible matches of the unknown sample to a reference sample.

In associated with another embodiment, for each respective reference sample identified as being a candidate match, the processing application as discussed herein generates probability information. The probability information can indicate information such as a degree to which the respective candidate reference sample is a relatively close match to the unknown sample under test. Thus, embodiments herein can include a multi-step process in which potential candidates are identified, and then a further analysis can be performed on the set of candidates to identify probability matches.

Certain embodiments herein include producing the probability information based at least in part on binary fixed-point arithmetic.

In accordance with further embodiments, if a respective candidate reference sample has a reasonably good chance of being a match to the unknown sample under test, further processing can be performed to determine which of the candidate reference samples is a best match to the unknown sample under test.

Comparing the peaks between the unknown sample and a respective reference sample can include identifying a subset of the multiple reference samples that are candidate matches to the unknown sample based on indexing of the peaks associated with the unknown sample into the multiple different sized range bins. Indexing as discussed herein can include any of the example techniques of identifying in which of multiple range bins peaks of the unknown sample reside.

By way of further non-limiting example, partitioning of the spectrum to include different sized range bins can include selecting boundaries of the different sized range bins in accordance with a hypergeometric distribution model.

Performing a search and/or generating the probability information can include implementing a hypergeometric probability function to generate probability information indicating whether or a degree to which the unknown sample matches a respective one of the multiple reference samples.

In accordance with yet another embodiment, the hypergeometric distribution uses collective properties of peak information associated with reference samples (e.g., known samples and respective peak data). Analysis as discussed herein can include calculating a probability that a respective peak match is a random event.

In accordance with further embodiments, the processing application as discussed herein can be configured to produce a string of symbols for the unknown sample. Via symbols such as logic ones or zeros in the string, the string for the unknown sample indicates in which of the multiple different sized range bins a respective peak of the unknown sample resides. The string for the unknown sample also can indicate in which of the multiple different sized range bins a respective peak of the unknown sample does not reside.

The processing application also can produce a respective string of symbols for each of the reference samples in a library of multiple reference samples. A respective string indicates in which of the multiple different sized range bins a peak of the respective reference sample resides. The respective string for the reference sample can also indicate in which of the multiple different sized range bins a peak of the respective reference sample does not reside.

In accordance with further embodiments, the processing application derives probability information based at least in part on a similarity between a binary string for the unknown sample and respective binary strings associated with the reference samples. That is, in general, the greater number of matches between the binary string for the unknown sample and the respective binary string associated with a corresponding reference sample, the greater the likelihood that the unknown sample matches the corresponding reference sample.

Indexing peaks associated with an unknown sample to the multiple different sized range bins can include, for each respective reference sample of the multiple reference samples: generating a value, k, the value k indicating a number of occurrences that a peak of the unknown sample falls into a bin in which the respective reference also includes a peak; generating a value, N, indicating a total number of the multiple different sized bins into which a spectrum is divided; generating a value, n, indicating a total number of peaks present in the respective reference sample; and generating a value, m, indicating a total number of peaks present in the unknown sample.

Based on the data as discussed above, embodiments herein include generating probability information (e.g., a p-value) for each of the respective reference samples based on the following example equation:

$$CDF(X = k) = f(k, N, m, n) = \sum_{i=0}^{k} \frac{\binom{m}{i}\binom{N-m}{n-i}}{\binom{N}{n}}$$

$$p\text{-value} = 1 - CDF$$

The lower the p-value, the more likely it is that the unknown sample is the same as the respective reference sample.

One embodiment herein includes computing a probability value to test a null hypothesis that an observed peak and/or reference bin match between the reference sample and a given reference sample occurred by chance.

By way of further non-limiting example, the application calculates a probability that a match between the peak in the unknown sample and the peak in the given reference sample to the particular range bin is a random event. As mentioned above, embodiments herein are advantageous over conventional techniques. For example, one embodiment herein includes a computationally efficient method of searching a library of reference samples to quickly narrow a number of candidates down to a smaller set of reference samples that more likely match the unknown sample under test. As mentioned, in one embodiment, a processing resource applies binary fixed-point arithmetic on a reduced number of data points to identify candidate matches. Certain searching operations as discussed herein are more than an order of magnitude faster than alternate computational approaches, and because the approach is probabilistic, the calculations maintain a high degree of accuracy.

Additional Embodiments

In a manner as discussed above, note that embodiments herein include generating and storing the peak and bin information. For example, as discussed above, spectral data processor can be configured to receive spectral information (e.g., indicating a set of peaks for each reference sample of multiple references samples). The spectral data processor partitions a spectrum to include multiple different sized range bins. Each of the peaks (as specified by the spectral information) in the multiple reference samples resides in one of the multiple different sized range bins. The spectral data processor stores peak information and bin information as peak and bin information. Stored peak and bin information includes bin information indicating the multiple different sized range bins generated for the partitioned spectrum. Stored peak information of the peak and bin information indicates in which of the multiple different sized range bins the peaks in the multiple reference samples reside.

In a manner as discussed above, note that embodiments herein include identifying possible matches between an unknown sample and the multiple reference samples. For example, as discussed above, analyzer application can be configured to access peak and bin information. More specifically, in one embodiment, the analyzer application receives range bin information (e.g., peak and bin information). The range bin information indicates multiple different sized range bins into which a spectrum has been partitioned. The analyzer application further receives peak information from peak and bin information. The peak information indicates a set of peaks associated with each of the multiple reference samples. The peak information further indicates in which of the multiple different sized range bins each of the peaks resides. To identify probable candidates that match the unknown sample, the analyzer application indexes locations of peaks associated with an unknown sample to the multiple different sized range bins.

These and other more specific embodiments are disclosed in more detail below.

Note that embodiments herein can include a configuration of one or more computerized devices, servers, base stations, wireless communication equipment, communication management systems, workstations, handheld or laptop computers, or the like to carry out and/or support any or all of the method operations disclosed herein. In other words, one or more computerized devices or processors can be programmed and/or configured to operate as explained herein to carry out different embodiments of the invention.

Yet other embodiments herein include software programs to perform the steps and operations summarized above and disclosed in detail below. One such embodiment comprises a computer program product including a non-transitory computer-readable storage medium (i.e., any computer readable hardware storage medium) on which software instructions are encoded for subsequent execution. The instructions, when executed in a computerized device having a processor, program and/or cause the processor to perform the operations disclosed herein. Such arrangements are typically provided as software, code, instructions, and/or other data (e.g., data structures) arranged or encoded on a non-transitory (i.e., non carrier wave) computer readable storage medium such as an optical medium (e.g., CD-ROM), floppy disk, hard disk, memory stick, etc., or other a medium such as firmware or shortcode in one or more ROM, RAM, PROM, etc., or as an Application Specific Integrated Circuit (ASIC), etc. The software or firmware or other such configurations can be installed onto a computerized device to cause the computerized device to perform the techniques explained herein.

Accordingly, embodiments herein are directed to a method, system, computer program product, etc., that supports operations as discussed herein.

For example, one embodiment includes a computer readable storage medium or computer readable hardware medium having instructions stored thereon. The instructions, when executed by a processor of a respective computer device, cause the processor or multiple processors to: receive a corresponding set of peaks for each reference sample of multiple references samples; partition a spectrum to include multiple different sized range bins, each of the peaks in the multiple reference samples residing in one of the multiple different sized range bins; and compare peaks associated with an unknown sample to the multiple different sized range bins.

In accordance with another embodiment, a computer readable storage medium or computer readable hardware medium includes instructions stored thereon. The instructions, when executed by a processor of a respective computer device, cause the processor or multiple processors to: receive range bin information, the range bin information indicating multiple different sized range bins into which a spectrum has been partitioned; receive peak information indicating a set of peaks associated with each of multiple reference samples, the peak information further indicating in which of the multiple different sized range bins each of the peaks resides; and index locations of peaks associated with an unknown sample to the multiple different sized range bins.

In accordance with yet another embodiment, a computer readable storage medium or computer readable hardware medium includes instructions stored thereon. The instructions, when executed by a processor of a respective computer device, cause the processor or multiple processors to: receive a set of peaks for each reference sample of multiple references samples; partition a spectrum to include multiple different sized range bins, each of the peaks in the multiple reference samples residing in one of the multiple different sized range bins; and store bin information indicating the multiple different sized range bins generated for the partitioned spectrum.

The ordering of the steps above has been added for clarity sake. These steps can be performed in any suitable order.

Other embodiments of the present disclosure include software programs and/or respective hardware to perform any of the method embodiment steps and operations summarized above and disclosed in detail below.

It is to be understood that the system, method, apparatus, instructions on computer readable storage media, etc., as discussed herein also can be embodied strictly as a software program, firmware, as a hybrid of software, hardware and/or firmware, or as hardware alone such as within a processor, or within an operating system or a within a software application.

As discussed herein, techniques herein are well suited for use in applications such as processing and use of spectral information. However, it should be noted that embodiments herein are not limited to use in such applications and that the techniques discussed herein are well suited for other applications as well.

Additionally, note that although each of the different features, techniques, configurations, etc., herein may be discussed in different places of this disclosure, it is intended, where suitable, that each of the concepts can optionally be executed independently of each other or in combination with each other. Accordingly, the one or more present inventions as described herein can be embodied and viewed in many different ways.

Also, note that this preliminary discussion of embodiments herein purposefully does not specify every embodiment and/or incrementally novel aspect of the present disclosure or claimed invention(s). Instead, this brief description only presents general embodiments and corresponding points of novelty over conventional techniques. For additional details and/or possible perspectives (permutations, elements, aspects, etc.) of the invention(s), the reader is directed to the textual Detailed Description section and corresponding figures of the present disclosure as further discussed below. The following Detailed Description, in addition to providing an intricate description of details of the invention, also provides a further summary of aspects of the invention or inventions.

BRIEF DESCRIPTION OF THE DRAWINGS

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles, concepts, etc.

FIG. 3 is an example chart illustrating peak information associated with each reference sample of multiple reference samples in a search pool according to embodiments herein.

FIG. 5 is an example diagram illustrating a chart of spectral information associated with an unknown sample under test and reference samples according to embodiments herein.

FIG. 6 is an example diagram illustrating generation of binary strings according to embodiments herein.

FIG. 7 is an example diagram illustrating count information associated with a comparison of peaks in the unknown sample to range bins according to embodiments herein.

DETAILED DESCRIPTION

By way of non-limiting example, a spectral processing application receives peak information associated with multiple references samples. The spectral processing application partitions a spectrum into multiple different sized range bins such that a substantially equal number of the peaks associated with the reference samples fall into each of the multiple different sized range bins. To identify candidate reference samples from a reference library database that potentially match an unknown sample under test, a searching application compares peaks associated with the unknown sample to the multiple different sized range bins. In general, the greater the number of bin matches between the unknown sample and a corresponding reference sample, the greater the likelihood that the unknown sample matches the corresponding reference sample.

Figure 1:
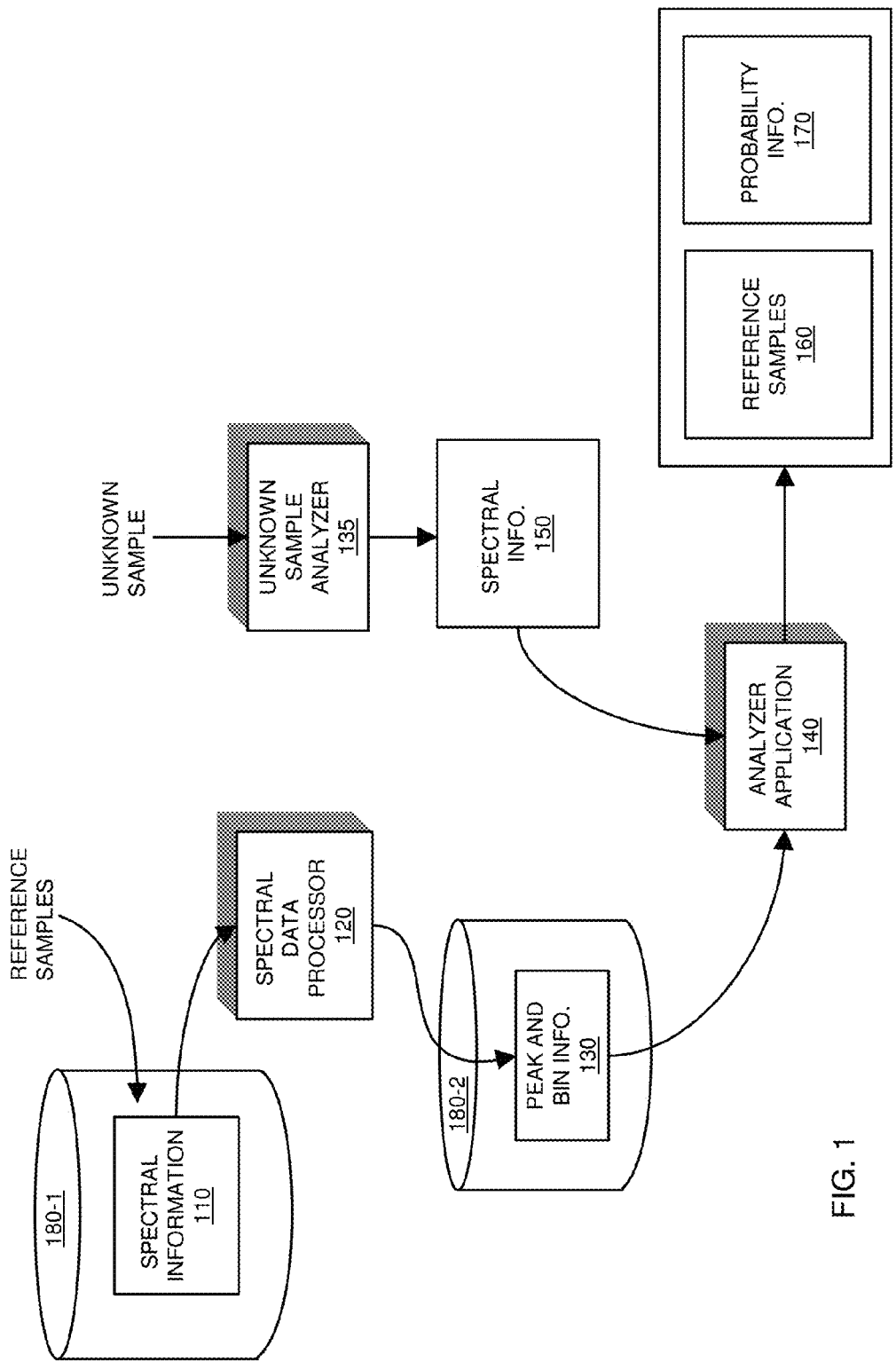
FIG. 1 is an example diagram illustrating a processing environment according to embodiments herein.

More specifically, FIG. 1 is an example diagram of a processing environment according to embodiments herein.

As shown, repository 180-1 stores a library of spectral information 110 derived from analyzing a pool of known reference samples. In one embodiment, the spectral information 110 indicates a spectral response derived during a respective analysis of each of the multiple reference samples. The spectral information 110 can be generated based on any suitable type of spectral analysis.

The spectral information 110 associated with the known reference samples 105 can be stored in any suitable format. For example, the spectral information 110 can indicate peaks associated with each of the references samples.

In other embodiments, the spectral information 110 can include a sweeping analysis of each of the reference samples. In this latter embodiment, the spectral information 110 for each of the known reference samples can include data such as multiple samples of data across a spectrum of wavelengths, peak information associated with a respective known reference sample, etc.

As discussed herein, spectral data processor 120 processes the spectral information 110 of the multiple known reference samples. Based on the processing, the spectral data processor 120 produces and stores peak and bin information 130 in repository 180-2.

In one embodiment, the spectral data processor 120 retrieves spectral information 110 from repository 180-1 and processes the spectral information 110 to identify the corresponding set of peaks for each of the multiple reference samples.

In comparison to the amount of storage needed to store the spectral information 110, the peak and bin information 130 stored in repository 180-2 can be compressed. In other words, the storage capacity required to store the spectral information 110 of multiple known reference samples can be substantially greater in size than the storage capacity needed to store the peak and bin information 130.

Embodiments herein can further include unknown sample analyzer 135. Unknown sample analyzer 135 analyzes the unknown sample and produces spectral information 150. Spectral information 150 includes peak information providing clues as to the identity of the unknown sample.

As discussed in further below, the analyzer application 140 compares spectral information 150 derived from analyzing the unknown sample to the peak and bin information 130 to produce candidate references 160 and corresponding probability information 170.

Thus, in contrast to conventional methods that merely identify a list of candidates that match an unknown sample under test, embodiments herein include converting and/or compressing the spectral information 110 of multiple known reference samples 110 into peak and bin information 130 and then generating probability information 170 indicating a degree to which the candidate references 160 are a good match to the unknown sample.

By way of a non-limiting example, in one embodiment, the analyzer application 140 is executed in a mobile, handheld field device. The handheld device may have limited processing and storage resources. The handheld device can be configured to store the peak and bin information 130 and perform the comparison of spectral information 150 to the reference samples to produce the candidate references 160 and the probability information 170.

Figure 2:
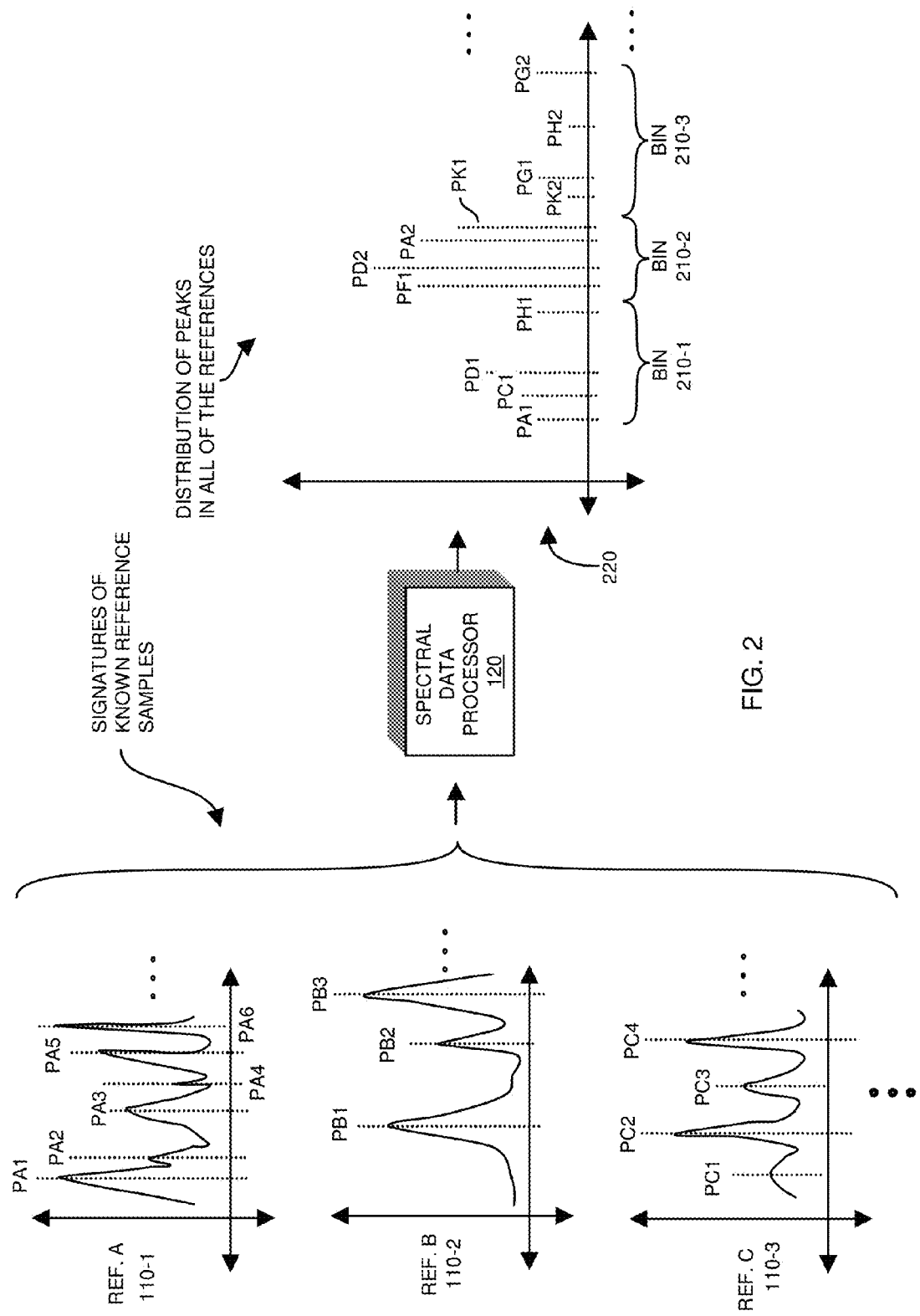
FIG. 2 is an example diagram illustrating processing of spectral information and generation of multiple range bins of varying width according to embodiments herein.

FIG. 2 is an example diagram illustrating conversion of the spectral information 110 of multiple known reference samples into peak and bin information 130 according to embodiments herein.

As shown, the spectral information 110 of multiple known reference samples can include: spectral information 110-1 derived from analyzing reference sample A, spectral information 110-2 derived from analyzing reference sample B, spectral information 110-3 derived from analyzing reference C, etc.

As previously mentioned, the spectral information 110 of multiple known reference samples 110 can be stored in any suitable form to represent results of a previous analysis. For example, the previous analysis of known reference sample A produces spectral information 110-1, the previous analysis of known reference sample B produces spectral information 110-2, the previous analysis of known reference sample C produces spectral information 110-3, and so on. Accordingly, peak information is known for each of the reference samples.

In this example, spectral information 110-1 associated with reference sample A includes peaks PA1, PA2, PA3, PA4, PA5, PA6, . . . ; spectral information 110-2 associated with reference sample B includes peaks PB1, PB2, PB3, . . . ; spectral information 110-3 associated with reference sample C includes peaks PC1, PC2, PC3, PC4, . . . ; and so on.

By way of a non-limiting example, the spectral data processor 120 processes the spectral information 110 of multiple known reference samples to identify a total number of peaks associated with a combination of all of the known reference samples. The spectral data processor 120 distributes all the peaks of the known reference samples on a single graph 220 as shown.

Subsequent to producing a distribution of the all of the peaks, the spectral data processor 120 then selects a width or size of each range bin 210 (e.g., range bin 210-1, range bin 210-2, range bin 210-3, etc.) such that a substantially equal number of peaks associated with the known reference samples reside in each of the range bins 210. For example, one embodiment herein includes identifying positions of all peaks in a database and then producing range bins of unequal width that will produce a uniform probability of observing a peak from the search database in any range bin.

Further details of how choosing the total number of range bins 210 for a respective distribution will be discussed later in this specification.

Assume that the peaks of the reference samples reside on x-axis as shown in FIG. 2. In this example, range bin 210-1 includes a peak associated with each of reference samples A, C, D, and H. For example, range bin 210-1 includes peak PA1 associated with reference sample A, peak PC1 associated with reference sample C, peak PD1 associated with reference sample D, and peak PH1 associated with reference sample H.

In this non-limiting example, range bin 210-2 includes a peak associated with reference samples F, D, A, and K. For example, range bin 210-2 includes peak PF1 associated with reference sample F, peak PD2 associated with reference sample D, peak PA2 associated with reference sample A, and peak PK1 associated with reference sample K.

Range bin 210-3 includes a peak associated with reference samples K, G, and H. For example, range bin 210-3 includes peak PK2 associated with reference sample K, peak PG1 associated with reference sample G, peak PH2 associated with reference sample H, and peak PG2 associated with reference sample G.

As mentioned, the distribution of the peaks associated with the known reference samples varies along the spectrum. For example, different portions of the spectrum include a different density of peaks because some reference samples produce peaks in the same region of the spectrum, while very few reference samples produce peaks in other parts of the spectrum.

As discussed herein, to account for the varying distribution of peaks in the spectrum, the spectral data processor 120 varies a width of the range bins 210 such that each range bin 210 includes a substantially equal number of peaks as each of the other range bins 210.

In one non-limiting example, the widths of the range bins 210 can be selected such that there are no gaps in the spectrum. For example, there is no space between range bin 210-1 and 210-2 because the left boundary of range bin 210-2 starts at or near the right boundary of range bin 210-1; the left boundary of range bin 210-3 starts at or near the right boundary of range bin 210-2; and so on.

In accordance with alternative embodiments, there may be a substantial portion of the spectrum that does not include a peak for any of the known reference samples. In such an instance, the widths of the range bins 210 can be selected such that respective portions of the spectrum are not included in a respective range bin. In other words, there can be a space or null gap between range bin 210-1 and range bin 210-2 where no peak resides; a space between range bin 210-2 and range bin 210-3 where no peak resides; and so on.

FIG. 3 is an example diagram illustrating a chart 300 of known reference samples and corresponding peak information according to embodiments herein.

Note that the chart 300 is presented for illustrative purposes only and that the number of reference samples in a library of known reference samples can vary depending on the embodiment.

In this example embodiment, the spectral information 110 of multiple known reference samples includes peak information associated with a pool of known reference samples A, B, C, D, E, F, G, H, J, and K.

As previously discussed, the spectral data processor 120 processes the spectral information 110 of multiple known reference samples to identify the corresponding peaks associated with each known reference sample.

Further in accordance with this example embodiment, based on the spectral information 110, the spectral data processor 120 identifies that known reference sample A includes 6 peaks including PA1, PA2, PA3, PA4, PA5, and PA6; the spectral data processor 120 identifies that known reference sample B includes 3 peaks including PB1, PB2, and PB3; the reference analyzer spectral data processor identifies that known reference sample C includes 5 peaks including PC1, PC2, PC3, PC4, and PC5; and so on.

As shown, there are a total of 40 peaks (e.g., peaks PA1, . . . , PA6, PB1, . . . , PB3, PC1, . . . , PC5, PD1, . . . , PD3, PE1, . . . PE4, . . . ) associated with the combination of known reference samples.

In this example, the spectral data processor 120 produces ten range bins including range bins 210-1, 210-2, 210-3, 210-4, 210-5, 210-6, 210-7, 210-8, 210-9, and 210-10.

As previously discussed, in FIG. 3, the spectral data processor 120 can split the spectrum into 10 range bins such that a substantially equal number of peaks falls into each range bin 210. There are 40 peaks associated with a combination of the known reference samples and ten range bins 210. Thus, in this non-limiting example, the spectral data processor 120 produces the width of each range bin 210 to include 4 peaks.

Figure 4:
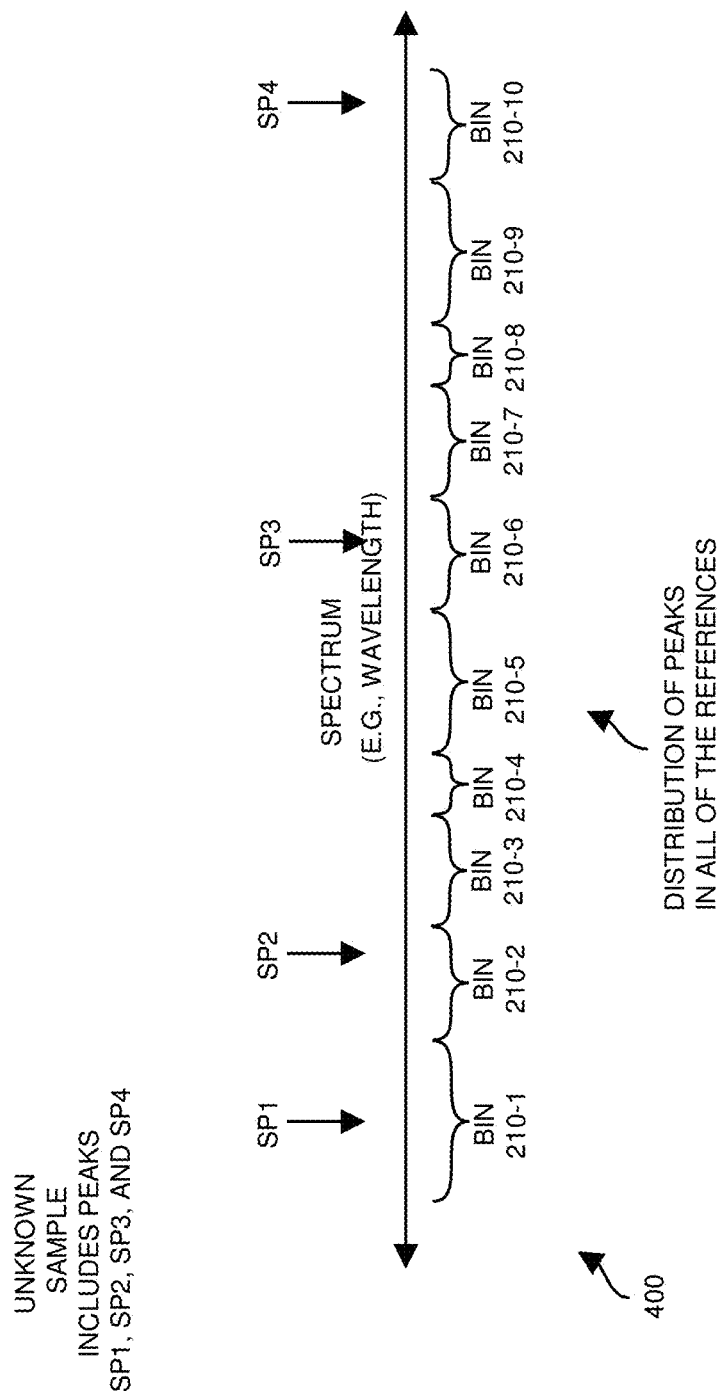
FIG. 4 is an example diagram illustrating indexing of peaks in an unknown sample to corresponding range bins according to embodiments herein.

FIG. 4 is an example diagram illustrating analysis of an unknown sample under test and indexing (i.e., comparing) of respective peaks of the unknown sample under test to multiple range bins according to embodiments herein. Note that a respective range bin can include multiple peaks for a given sample. For example, range bin 210-3 includes peak PG1 and peak PG2; and so on.

In this example, assume that the unknown sample under test produces 4 peaks when analyzed. In this example, the unknown sample under test includes peak SP1, peak SP2, peak SP3, and peak SP4. Each of the peaks associated with the unknown sample under test falls at a particular location along the x-axis in the spectrum illustrated as graph 400.

As shown, in furtherance of generating probability information 170, the application 140 indexes the peak SP1, peak SP2, peak SP3, and peak SP4 to corresponding range bins 210. In this example embodiment, peak SP1 falls within range bin 210-1; peak SP2 falls within range bin 210-2; peak SP3 falls within range bin 210-6; and peak SP4 falls within range bin 210-10.

Note that the step of indexing as discussed herein can include any of the example techniques of identifying, mapping, matching, etc., in which of multiple range bins peaks of the unknown sample reside.

FIG. 5 is an example diagram illustrating a further example of indexing peaks associated with an unknown sample under test to candidate reference samples according to embodiments herein.

By way of a non-limiting example, the application 140 produces a binary string 510 for the unknown sample. The binary string 510 indicates in which of the ten bins (e.g., 210-1, . . . , 210-10) a respective peak of the unknown sample under test resides.

In this example, the first binary value (e.g., leftmost bit location) in the binary string 510 is set to a value of 1 indicating that the unknown sample under test includes a peak value (e.g., SP1) in the respective range bin 210-1; the second binary value in the binary string 510 is set to a value of 1 indicating that the unknown sample under test includes a peak value (e.g., SP2) in the respective range bin 210-2; the third binary value in the binary string 510 is set to a value of 0 indicating that the unknown sample under test does not include a peak value in the respective range bin 210-3; the fourth binary value in the binary string 510 is set to a value of 0 indicating that the unknown sample under test does not include a peak value in the respective range bin 210-4; the fifth binary value in the binary string 510 is set to a value of 0 indicating that the unknown sample under test does not include a peak value in the respective range bin 210-5; the sixth binary value in the binary string 510 is set to a value of 1 indicating that the unknown sample under test includes a peak value (e.g., SP3) in the respective range bin 210-6; the seventh binary value in the binary string 510 is set to a value of 0 indicating that the unknown sample under test does not include a peak value in the respective range bin 210-7; the eighth binary value in the binary string 510 is set to a value of 0 indicating that the unknown sample under test does not include a peak value in the respective range bin 210-8; the ninth binary value in the binary string 510 is set to a value of 0 indicating that the unknown sample under test does not include a peak value in the respective range bin 210-9; and the tenth binary value (e.g., rightmost bit location) in the binary string 510 is set to a value of 1 indicating that the unknown sample under test includes a peak value (e.g., SP4) in the respective range bin 210-10.

Accordingly, the binary string 510 provides an indication of which range bins a peak of the unknown sample resides.

As further shown in FIG. 5, the application can be configured to identify which of the multiple known reference samples are better or best candidates that potentially match the unknown sample under test. As an example, any known reference samples having a peak falling in the same range bin as a range bin in which at least one peak of the unknown sample under test also resides indicates a candidate (known) reference sample that may match the unknown sample under test.

The more peaks of the unknown sample under test that fall into the same range bins as a respective known reference sample, the more likely it is that the respective known reference sample matches the unknown sample under test. As further discussed below, if there is no bin overlap between the unknown sample under test and the known reference sample, the more likely it is that the respective known reference sample is not a match to the unknown sample under test.

FIG. 6 is an example diagram illustrating generation of a respective binary string for each of the known reference samples according to embodiments herein.

By way of a non-limiting example, the peak and bin information 130 can include the binary strings 610 associated with the known reference samples.

As shown, embodiments herein include producing a binary string for each of the known reference samples. For example, the binary string 610-1 indicates in which of the ten bins (e.g., 210-1, . . . , 210-10) a respective peak of the known reference sample A resides.

In this example, the first binary value (e.g., leftmost bin location) in the binary string 610-1 is set to a value of 1 indicating that the known reference sample A includes a peak value (e.g., PA1) in the respective range bin 210-1; the second binary value in the binary string 610-1 is set to a value of 1 indicating that the known reference sample A includes a peak value (e.g., PA2) in the respective range bin 210-2; the third binary value in the binary string 610-1 is set to a value of 0 indicating that the known reference sample A does not include a peak value in the respective range bin 210-3; the fourth binary value in the binary string 610-1 is set to a value of 0 indicating that the known reference sample A does not include a peak value in the respective range bin 210-4; the fifth binary value in the binary string 610-1 is set to a value of 1 indicating that the known reference sample A includes a peak value (e.g., PA3) in the respective range bin 210-5; the sixth binary value in the binary string 610-1 is set to a value of 1 indicating that the known reference sample A includes a peak value (e.g., PA4) in the respective range bin 210-6; the seventh binary value in the binary string 610-1 is set to a value of 1 indicating that the known reference sample A does include a peak value (e.g., PA5) in the respective range bin 210-7; the eighth binary value in the binary string 610-1 is set to a value of 0 indicating that the known reference sample A does not include a peak value in the respective range bin 210-8; the ninth binary value in the binary string 610-1 is set to a value of 0 indicating that the known reference sample A does not include a peak value in the respective range bin 210-9; and the tenth binary value (e.g., rightmost bit location) in the binary string 610-1 is set to a value of 1 indicating that the known reference sample A includes a peak value (e.g., PA6) in the respective range bin 210-10.

Accordingly, the binary string 610-1 provides an indication of which range bins 210 one or more peaks of the known sample A reside.

In furtherance of this example, the first binary value (e.g., leftmost bin location) in the binary string 610-2 is set to a value of 1 indicating that the known reference sample C includes a peak value (e.g., PC1) in the respective range bin 210-1; the second binary value in the binary string 610-2 is set to a value of 0 indicating that the known reference sample C does not include a peak value in the respective range bin 210-2; the third binary value in the binary string 610-2 is set to a value of 0 indicating that the known reference sample C does not include a peak value in the respective range bin 210-3; the fourth binary value in the binary string 610-2 is set to a value of 1 indicating that the known reference sample C does include a peak value (e.g., PC2) in the respective range bin 210-4; the fifth binary value in the binary string 610-2 is set to a value of 0 indicating that the known reference sample C does not include a peak value (e.g., PC2) in the respective range bin 210-5; the sixth binary value in the binary string 610-2 is set to a value of 1 indicating that the known reference sample C includes a peak value (e.g., PC3) in the respective range bin 210-6; the seventh binary value in the binary string 610-2 is set to a value of 0 indicating that the known reference sample C does not include a peak value in the respective range bin 210-7; the eighth binary value in the binary string 610-2 is set to a value of 1 indicating that the known reference sample C does include a peak value (e.g., PC4) in the respective range bin 210-8; the ninth binary value in the binary string 610-2 is set to a value of 0 indicating that the known reference sample C does not include a peak value in the respective range bin 210-9; and the tenth binary value (e.g., rightmost bit location) in the binary string 610-2 is set to a value of 1 indicating that the known reference sample C includes a peak value (e.g., PC5) in the respective range bin 210-10.

Accordingly, the binary string 610-2 provides an indication of which range bins 210 one or more peaks of the known sample C reside.

In this way, each of the strings 610 (e.g., string 610-1, string 610-2, string 610-3, string 610-4, string 610-5, ...) in chart 600 indicates in which bin a respective one or more peaks of the known sample resides.

FIG. 7 is an example diagram illustrating a chart of comparison information according to embodiments herein.

As previously discussed, the application 140 generates a binary string 510 associated with the unknown sample under test. The application 140 compares the binary string 510 associated with the unknown sample under test to each of the binary strings 610 to populate the chart 700 with relevant count data.

Chart 700 includes values k, N, m, and n.

Value k represents the number of range bins in which both the unknown sample under test and the respective reference sample each include at least one corresponding peak.

Value N represents a total number of range bins into which the spectrum is divided.

Value m represents the number of peaks in the unknown reference sample.

Value n represents the number of peaks in the respective reference sample.

Calculating Probability Information

By way of a non-limiting example, the application 140 can generate probability information as discussed below.

As mentioned, after a binary test spectrum (e.g., binary string 510) is available, it is compared in sequence to each of the reference binary peak spectra (e.g., binary strings 610). During each comparison (i.e., unknown vs Ref A, unknown vs Ref B, etc.), the number of peak matches between the two spectra being compared is recorded.

In one embodiment, the hypergeometric probability mass function below produces the probability of finding k matches, by chance, between an unknown spectrum (e.g., binary string 510) containing m peaks and a reference spectrum (e.g., binary string 610) containing n peaks for a database containing N bins.

$$P(X = k) = \frac{\binom{m}{k}\binom{N-m}{n-k}}{\binom{N}{n}} \quad \text{equation 1}$$

In equation 1 above, $$\binom{m}{k}$$

represents a binomial coefficient (which is often read as m choose k). One method for computing the binomial coefficient is to use the factorial formula:

$$\binom{m}{k} = \frac{m!}{k!(m-k)!} \quad \text{equation 2}$$

In order to rule out a reference material (e.g., reference sample) as being part of the measured unknown sample, the hypergeometric cumulative distribution function is used to compute a p-value and test the null hypothesis that the observed matches occurred by chance.

$$CDF(X = k) = f(k, N, m, n) = \sum_{i=0}^{k} \frac{\binom{m}{i}\binom{N-m}{n-i}}{\binom{N}{n}} \quad \text{equation 3}$$

In one embodiment, the p-value is calculated as 1-CDF (X=k), and any p-value <0.05 can be used to reject the null hypothesis with 95% confidence.

Looking at the p-values in the chart 700 in FIG. 7, the results make sense: only one match out of 3 or 4 peaks results in a higher p-value (known reference sample H), matching all or nearly all of the peaks in the unknown with a reference produces a relatively low p-value (known reference sample D), and matching a few peaks when there are many peaks in both the respective reference sample and unknown sample under test produces high p-values (known reference sample K).

As discussed below, based on the values k, N, m, and n, the application 140 generates p-values for each of the known reference samples.

More specifically, when comparing the binary string 510 to the binary string 610-1, the application 140 identifies that there are k=4 common range bins (e.g., range bin 210-1, range bin 210-2, range bin 210-6, and range bin 210-10) between the known reference sample A and the unknown sample under test. For example, there are 4 range bins including a peak form both the unknown sample under test and the reference sample.

The application 140 identifies that there are a total of N=10 range bins (e.g., range bin 210-1, ..., range bin 210-10).

The application 140 identifies that there are m=4 peaks in the unknown sample under test.

The application 140 identifies that there are n=6 peaks in the respective reference sample A.

Based on this information and the above equation 3, the application generates probability information indicating whether reference sample A is a good match to the unknown sample under test.

In this example, the application 140 generates the p-value of 0.0714 using the above values and equations. This relatively low p-value indicates that the known reference sample A is a reasonably good match candidate for the unknown sample under test.

When comparing binary string 510 and binary string 610-2, the application 140 identifies that there are k=0 common range bins between the known reference sample B and the unknown sample under test. The application 140 identifies that there are a total of N=10 range bins (e.g., range bin 210-1, . . . , range bin 210-10). The application 140 identifies that there are m=4 peaks in the unknown sample under test. The application 140 identifies that there are n=6 peaks in the respective reference sample A.

Based on this information, the application generates probability information indicating whether reference sample B is a good match to the unknown sample under test. In this example, the application generates the p-value of 1.0. This high p-value indicates that the known reference sample B is not a good match candidate.

When comparing binary string 510 and binary string 610-3, the application 140 identifies that there are k=3 common range bins (e.g., range bin 210-1, range bin 210-6, range bin 210-10) between the known reference sample C and the unknown sample under test. The application 140 identifies that there are a total of N=10 range bins (e.g., range bin 210-1, . . . , range bin 210-10). The application 140 identifies that there are m=4 peaks in the unknown sample under test. The application 140 identifies that there are n=5 peaks in the respective reference sample C.

Based on this information, the application generates probability information indicating whether reference sample C is a good match to the unknown sample under test. In this example, the application generates the p-value of 0.0333 for reference sample C. This relatively low p-value indicates that the known reference sample C is a very good match candidate for the unknown sample under test. In other words, the unknown sample under test is likely the same type as the known reference sample C.

In this manner, the application compares each of the binary strings 610 to the binary string 510 associated with the unknown sample under test. The application 140 produces a respective p-value for each of the unknown reference samples. As mentioned, the p-value indicates a degree to which the unknown sample under test matches a respective known reference sample in the library. This information can be displayed to a respective user to notify the user subset of all of the references samples are best matches to the unknown sample under test.

Figure 8:
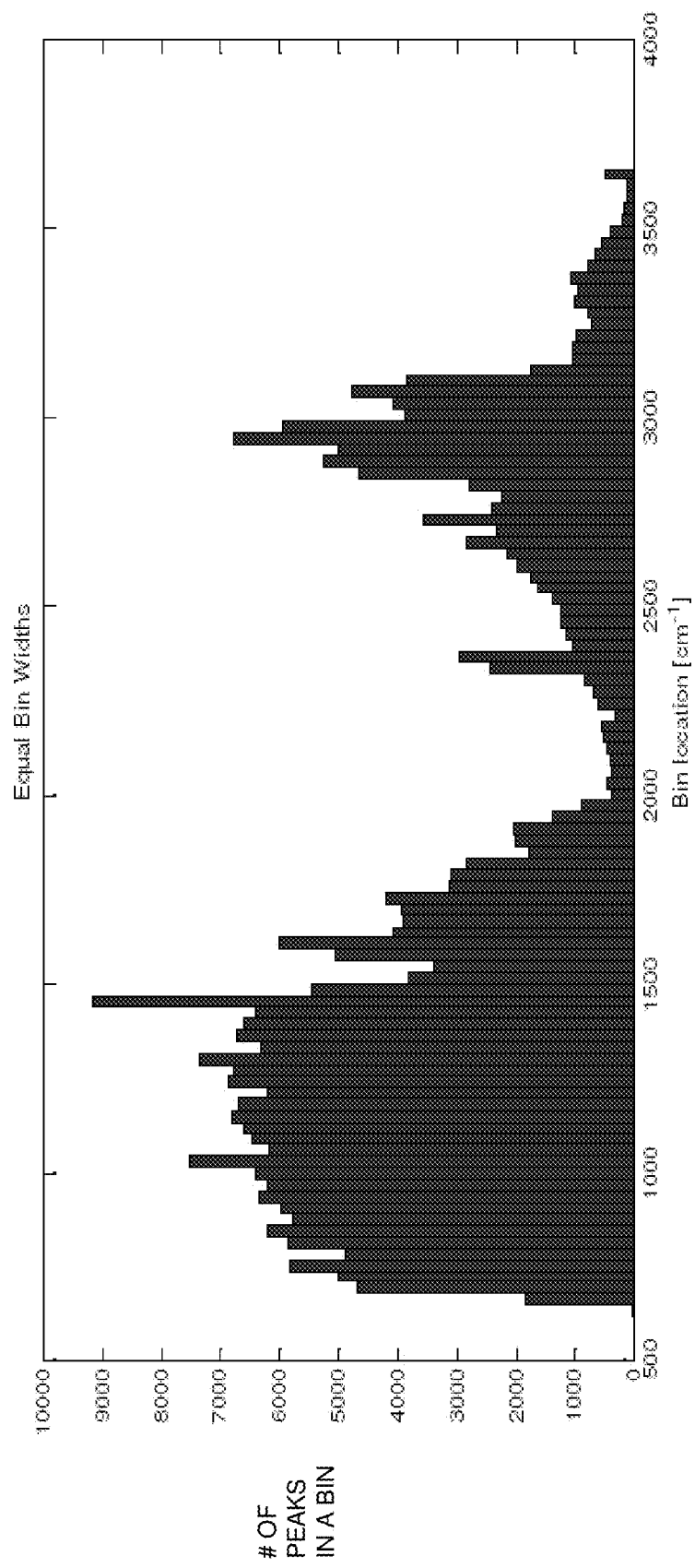
FIG. 8 is an example diagram illustrating partitioning of a spectrum to include multiple range bins of equal width.

FIG. 8 is an example graph 800 illustrating partitioning of a spectrum into equal sized range bins for a library of many reference samples.

The x-axis of graph 800 indicates a wavelength or other suitable spectral measurement value. The y-axis of graph 800 indicates a number of counts or number of peaks that occur for each respective bin. The graph 800 has been generated based on an Infrared spectral database of 10,000 chemicals. For example, the spectral distribution of 322,468 peaks (associated with the 10,000 sample chemicals) from this reference sample database has been divided into 50 range bins of equal width.

As shown in FIG. 8, the peak information associated with library of reference samples is more and less dense across the wavelength spectrum on the x-axis of graph 800. That is, the number of peaks in each equal sized bin is very non-uniform when choosing equal sized range bins.

In general, there is a higher occurrence of peaks associated with reference samples between 1000 and 1500 than there are occurrence of peaks associated with reference samples between 2000 and 2500 on the x-axis. Thus, merely partitioning a spectrum into equal widths produces range bins having a different number of peaks.

Figure 9:
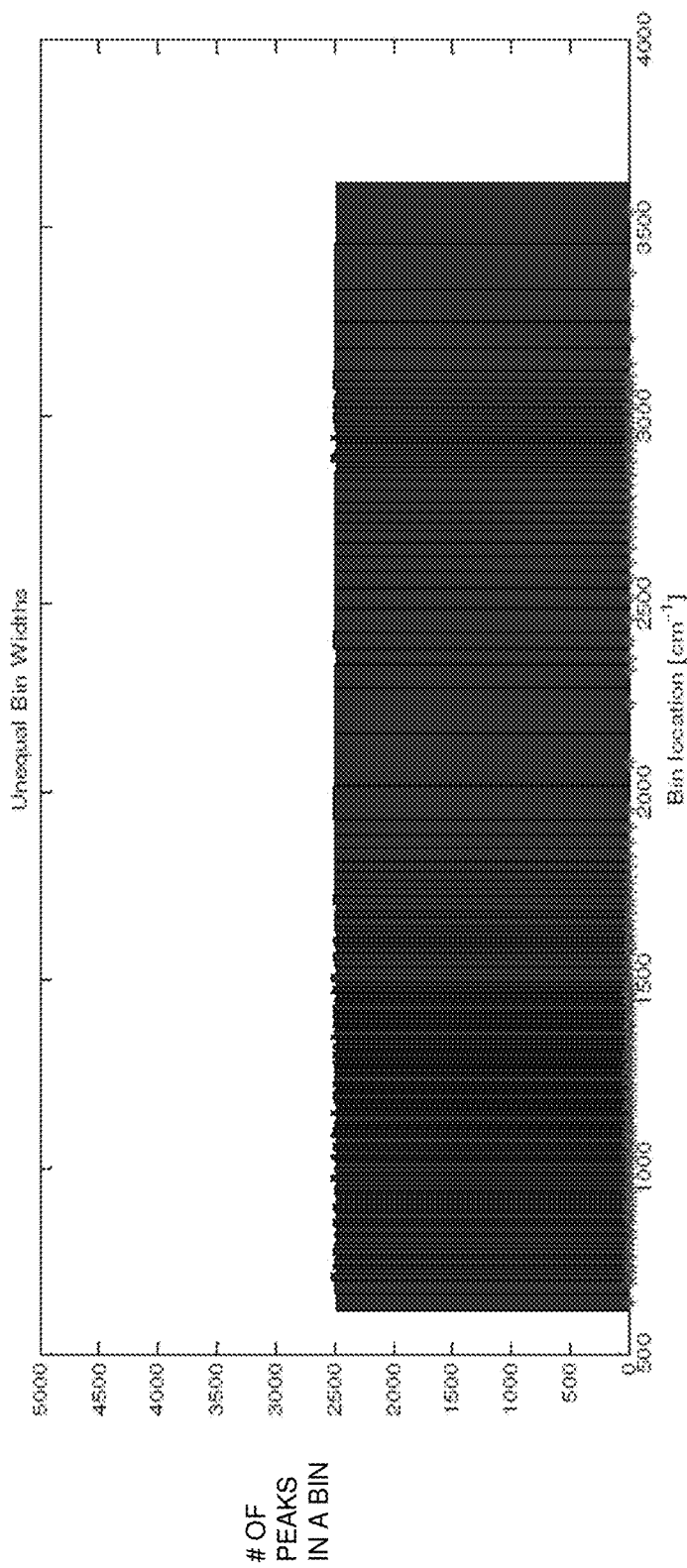
FIG. 9 is an example diagram illustrating partitioning of a spectrum to include multiple range bins of varying width according to embodiments herein.

FIG. 9 is an example graph 900 illustrating partitioning a spectrum into unequal sized range bins according to embodiments herein. The x-axis of graph 900 indicates a parameter such as a wavelength-based value. The y-axis of graph 900 indicates a parameter such as a number of counts or number of peaks that occur for each respective bin.

As previously discussed, the distribution of peak information associated with library of reference samples is more and less dense across the spectrum on the x-axis of graph 900. However, as previously discussed, embodiments herein include partitioning the spectrum (e.g., wave number, wavelength, frequency, m/z, etc.) into different sized range bins such that a substantially equal number of peaks associated with reference samples resides in any given range bin.

As noted above, one embodiment herein includes characterizing peaks associated with reference samples in a library to determine bin locations that will produce a uniform probability of observing a peak from the search database in any bin. As mentioned above, producing the different sized range bins can include starting from one edge of the spectrum and determining how wide the first bin (e.g., leftmost bin in the spectrum) must be such that the desired occurrence of peaks (e.g., X peaks) associated with the reference samples falls within the first bin.

From a rightmost boundary of the first bin (which potentially defines a left boundary of the second bin), embodiments herein can further include analyzing the peak information associated with the reference samples in the spectrum to identify how wide the second range bin needs to be such that the second range bins includes the next X peaks in the spectrum. This process is repeated to divide the spectrum into a desired number of range bins, each of the range bins including a substantially equal number of peaks associated with the reference samples.

By way of a non-limiting example, this procedure of dividing the spectrum can be carried out for the reference samples such that there is a Y % chance of observing a peak in any bin using any reference spectrum. The graph 900 is a histogram demonstrating that appropriate sizing of the different range bins results in a relatively uniform distribution of the peaks (i.e., each range includes approximately the same number of peaks).

In accordance with yet a further embodiment, it should be noted, however, that when the hypergeometric distribution is used, a respective range bin containing more than one peak for a sample can be represented in the same way as a bin containing a single peak for the sample. For example, in one embodiment, during analysis, a bin having a single peak for a respective reference sample would be assigned a binary value of 1; a bin having multiple peaks for the respective reference sample also would be assigned a binary value of 1 as well.

In accordance with alternative embodiments, note that other distribution functions could be used to allow assignment of more than 2 values (e.g., a binary 0 or a binary 1) per bin. For example, the number assigned to the string for a given range bin can indicate a value of 2 if there were two peaks in the corresponding sample that fell in the range bin; the number assigned to the string for a given range bin can indicate a value of 3 if there were three peaks in the corresponding sample that fell in the range bin; and so on.

Additional Embodiments

In accordance with another embodiment, if more than one peak from a spectrum falls in the same bin, then a multivariate hypergeometric distribution can be used to determine the peak matching probability. For example, if there are either no, one or two peaks per bin, then the probability of matching k1 one-peak bins and k2 two-peak bins is $$P(X_1 = k_1, X_2 = k_2) =$$

$$f(k_1, k_2 N, m_1, m_2, n_1, n_2) = \frac{\binom{m_1}{k_1}\binom{m_2}{k_2}\binom{N - m_1 - m_2}{n_1 - k_1 + n_2 - k_2}}{\binom{N}{n_1 + n_2}}$$

This can be extended to three or more peaks per bin using the same formulation.

Figure 10:
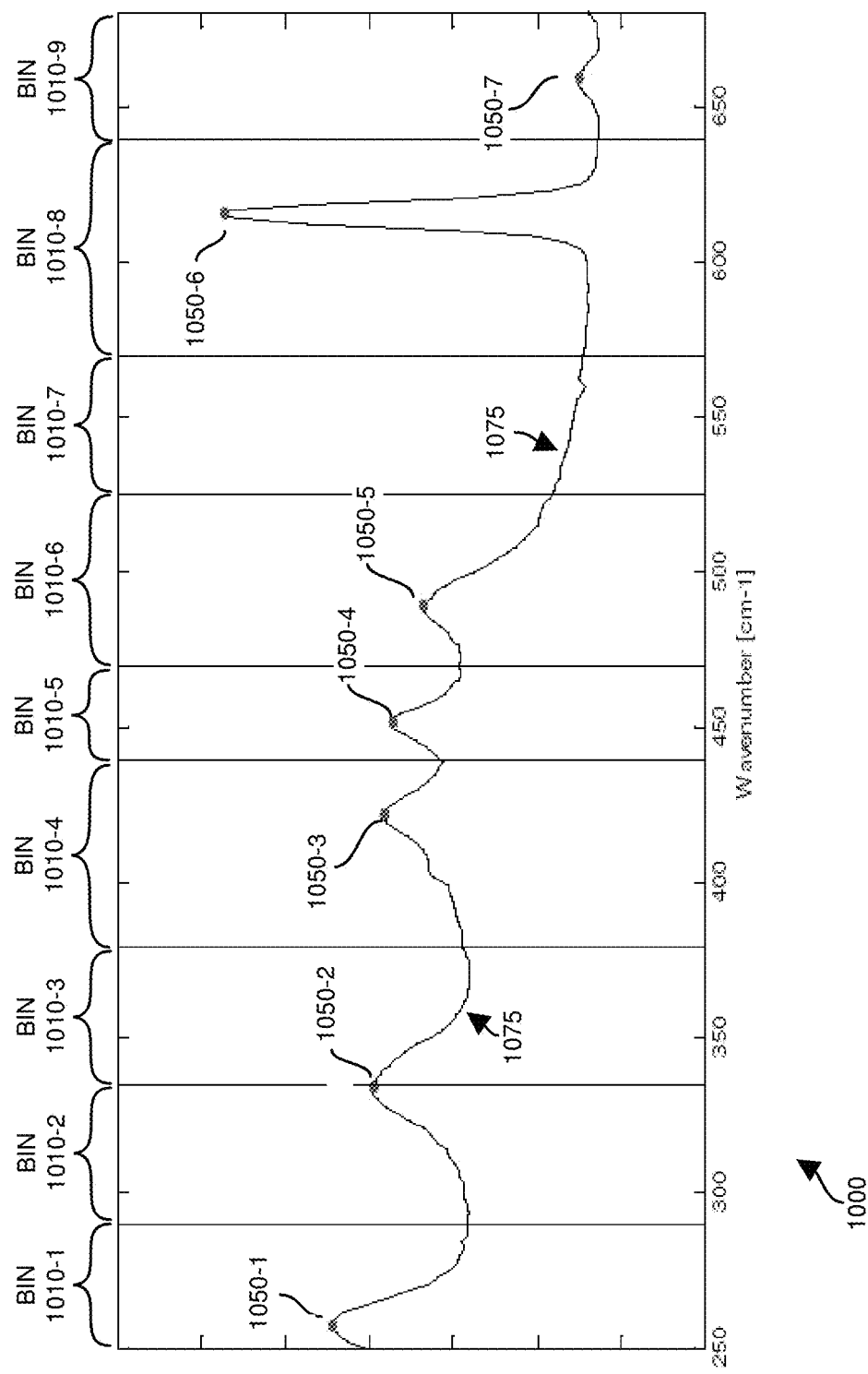
FIG. 10 is an example diagram illustrating peak information associated with an unknown sample according to embodiments herein.

FIG. 10 is an example diagram illustrating an example of processing according to embodiments herein.

Note that a special case occurs for peaks that are observed within the wavelength error of more than one bin. In other words, the estimated peak location will be a single value, but location+/−wavelength accuracy may lie within more than one bin. When this occurs, embodiments herein can include creating more than one binary string for the sample (corresponding to flipping the peak location between the two bins in question), or allowing a single peak to occupy more than one bin. In one embodiment, the application 140 does this for test spectra (e.g., unknown sample under test), but not for reference spectra (e.g., reference samples).

As shown, in this example, assume that analysis of the unknown sample under test produces spectral information 1075. The unknown sample under test includes a peak value 1050-2 that falls between range bin 1010-2 and range bin 1010-3. Other peak values associated with the unknown sample as indicated by spectral information 1075 generally do not lie near an edge of a range bin and therefore are included in a single range bin.

Processing associated with this type of condition (e.g., peak 1050-2 on the edge of two range bins) can be handled in a number of ways. For example, one embodiment herein includes assigning the peak 1050-2 to both range bin 1010-2 and range bin 1010-3 and then performing the analysis as discussed above. In this instance, the processing application performs an analysis in which the binary string is 111111011 (e.g., peak value 1050-1 resides in range bin 1010-1; peak value 1050-2 resides in range bin 1010-2; peak value 1050-2 resides in range bin 1010-3; peak value 1050-3 resides in range bin 1010-4; peak value 1050-4 resides in range bin 1010-5; peak value 1050-5 resides in range bin 1010-6; peak value 1050-6 resides in range bin 1010-8; peak value 1050-7 resides in range bin 1010-9). The probability information for the sample is generated in a manner as discussed above.

In an alternative embodiment, the processing application can perform multiple separate processing passes including a first pass and a second pass. On the first pass, the processing application assigns the peak value 1050-2 to the range bin 1010-2 (and not range bin 1010-3) and produces the probability information for the unknown sample under test in a manner as discussed above based on the string 110111011. On the second pass, the processing application assigns the peak value 1050-2 to the range bin 1010-3 (and not range bin 1010-2) and produces the probability information for the unknown sample under test in a manner as discussed above based on the string 101111011.

Figure 11:
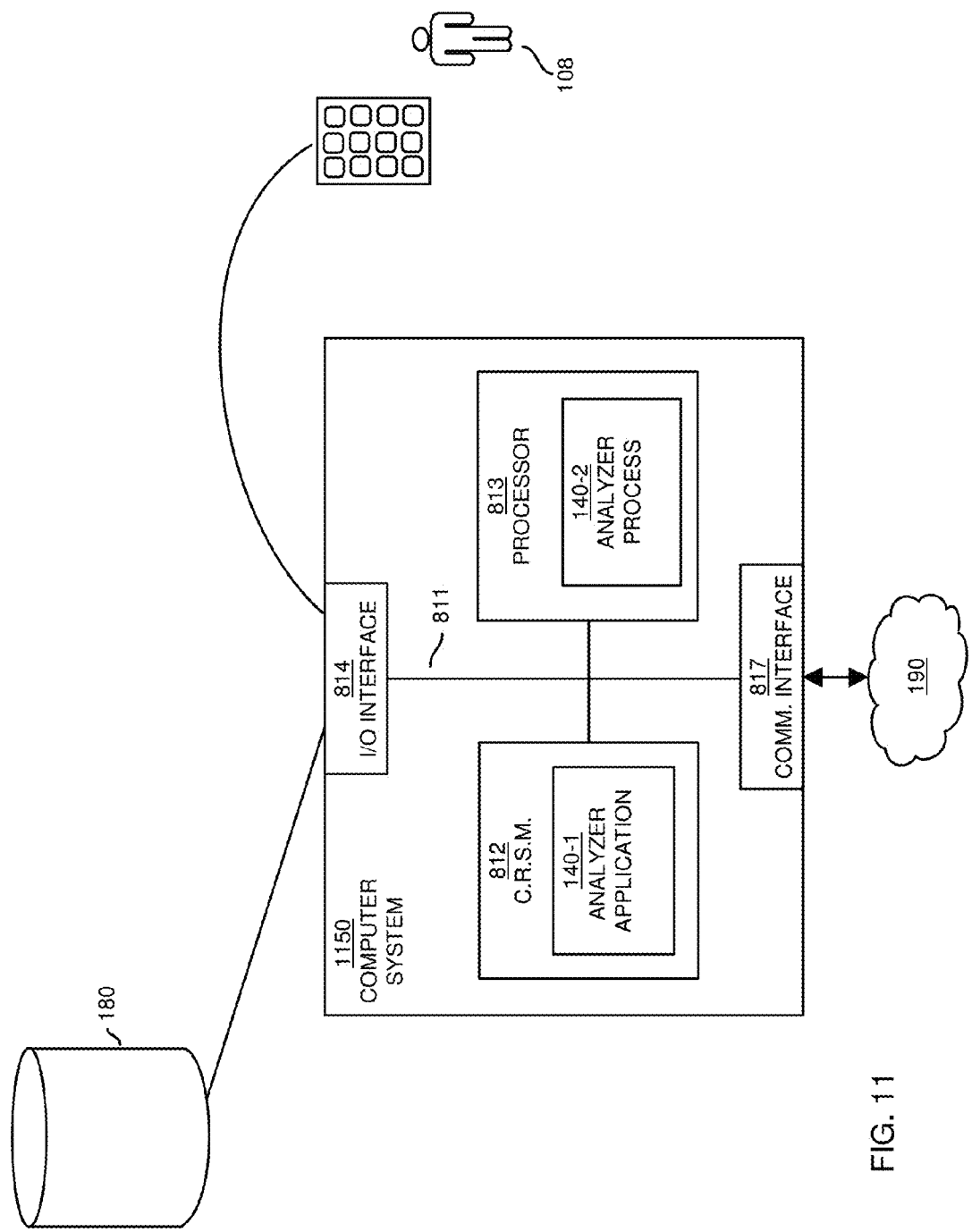
FIG. 11 is a diagram illustrating example architecture on which to execute methods according to embodiments herein.

FIG. 11 is an example block diagram of a computer system 1150 for implementing any of the operations according to embodiments herein.

As shown, computer system 1150 of the present example can include an interconnect 811 that couples computer readable storage media 812 such as a non-transitory type of media (i.e., any type of hardware storage medium) in which digital information can be stored and retrieved, a processor 813, I/O interface 814, and a communications interface 817.

I/O interface 814 provides connectivity to a repository 180 (e.g., repository 180-1, repository 180-2, etc.) and, if present, other devices such as display screen, keypad, a computer mouse, etc.

Computer readable storage medium 812 can be any non-transitory storage device such as memory, optical storage, hard drive, floppy disk, etc. In one embodiment, the computer readable storage medium 812 stores instructions and/or data.

Communications interface 817 enables the computer system 1500 and processor 813 to communicate over a resource such as network 190 to retrieve information from remote sources and communicate with other computers. Depending on the embodiment, any or all of the functionality associated with the analyzer application 140-1 can be performed locally by processor 813, or via resources in network 190, or a combination of both.

I/O interface 814 enables processor 813 to retrieve or attempt retrieval of stored information from repository 180.

As shown, computer readable storage media 812 is encoded with analyzer application 140-1 (e.g., software, firmware, etc.) executed by processor 813. Analyzer application 140-1 can be configured to include instructions to implement any of the operations associated with analyzer application 140 as previously discussed.

During operation of one embodiment, processor 813 accesses computer readable storage media 812 via the use of interconnect 811 in order to launch, run, execute, interpret or otherwise perform the instructions in analyzer application 140-1 stored on computer readable storage medium 812.

Execution of the analyzer application 140-1 produces processing functionality such as analyzer process 140-2 in processor 813. In other words, the analyzer process 140-2 associated with processor 813 represents one or more aspects of executing analyzer application 140-1 within or upon the processor 813 in the computer system 1150.

Those skilled in the art will understand that the computer system 1150 can include other processes and/or software and hardware components, such as an operating system that controls allocation and use of hardware resources to execute analyzer application 140-1.

In accordance with different embodiments, note that computer system may be any of various types of devices, including, but not limited to, a personal computer system, a wireless device, base station, phone device, desktop computer, laptop, notebook, netbook computer, mainframe computer system, handheld computer, workstation, network computer, application server, storage device, a consumer electronics device such as a camera, camcorder, set top box, mobile device, video game console, handheld video game device, a peripheral device such as a switch, modem, router, or in general any type of computing or electronic device. The computer system 1150 and/or functionality supported by the analyzer application 140 may reside or be moved to any location.

Computer system 1150 or a similar type of architecture can be used to implement the spectral data processor 120.

Functionality supported by the spectral data processor 120 and/or the analyzer application 140 will now be discussed via flowcharts in FIGS. 12-14. Note that the steps in the flowcharts below can be executed in any suitable order and further summarize the embodiments as discussed herein.

Figure 12:
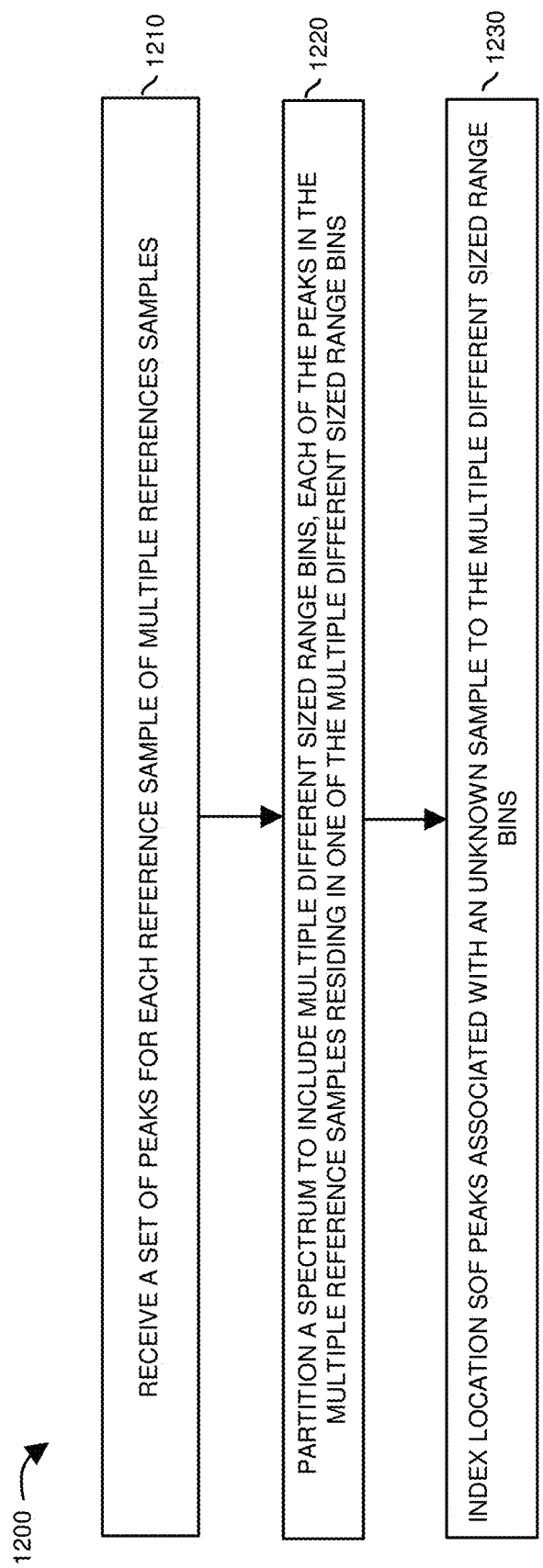
FIGS. 12-14 are flowcharts illustrating example methods according to embodiments herein.

FIG. 12 is a flowchart 1200 illustrating an example method according to embodiments herein. Note that there will be some overlap with respect to concepts as discussed above.

In step 1210, the spectral data processor 120 identifies and/or receives spectral information of multiple known reference samples 110. In one embodiment, the spectral information 110 of multiple known reference samples includes data specifying a set of peaks for each reference sample of multiple references samples.

In step 1220, the spectral data processor 120 partitions a spectrum to include multiple different sized range bins 210. In one embodiment, the spectral data processor 120 partitions the spectrum such that each of the peaks in the multiple reference samples resides in one of the multiple different sized range bins 210.

In step 1230, the application 140 indexes (e.g., compares, maps, etc.) locations of peaks associated with an unknown sample to the multiple different sized range bins 210.

Figure 13:
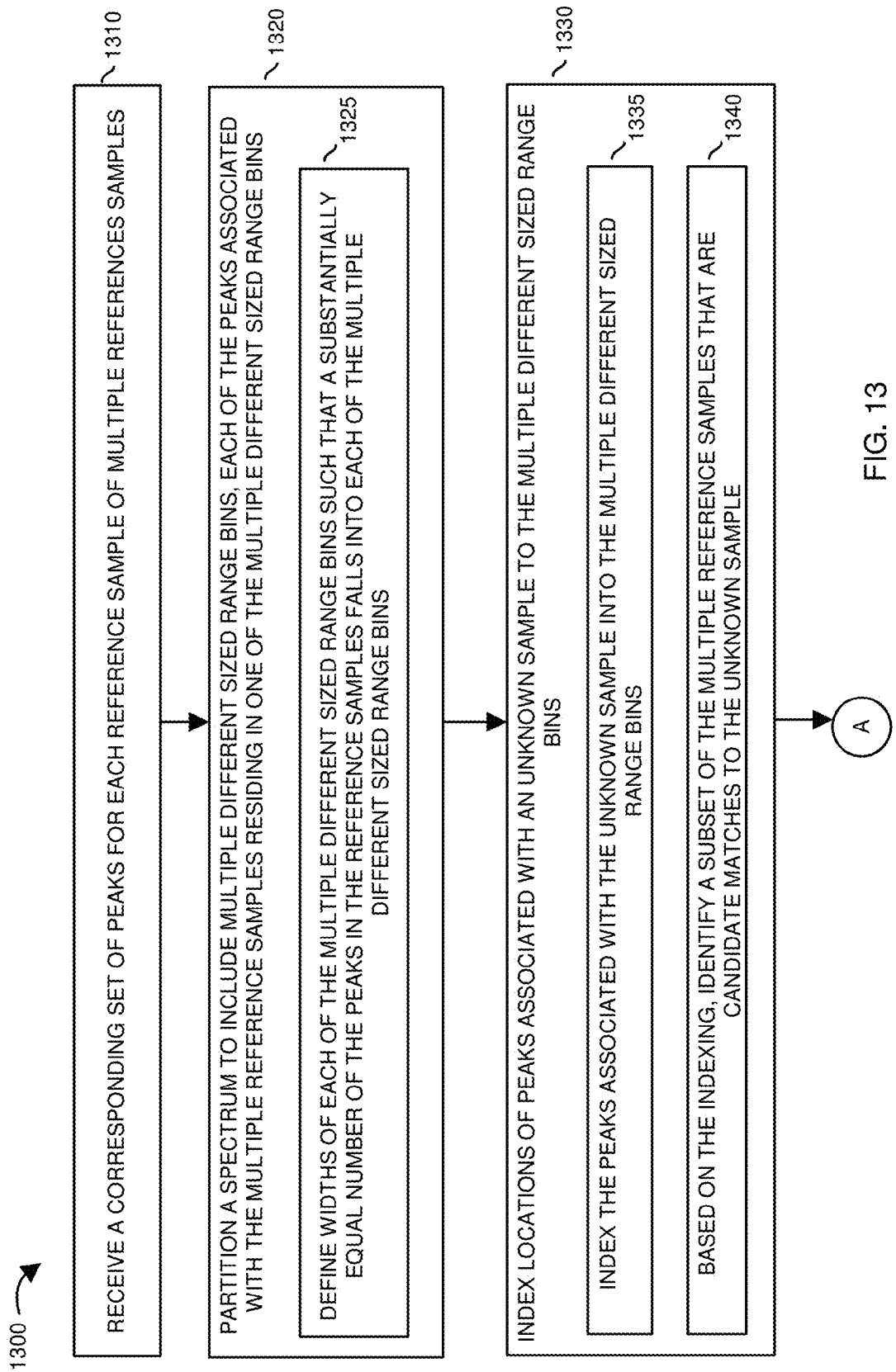
Figure 14:
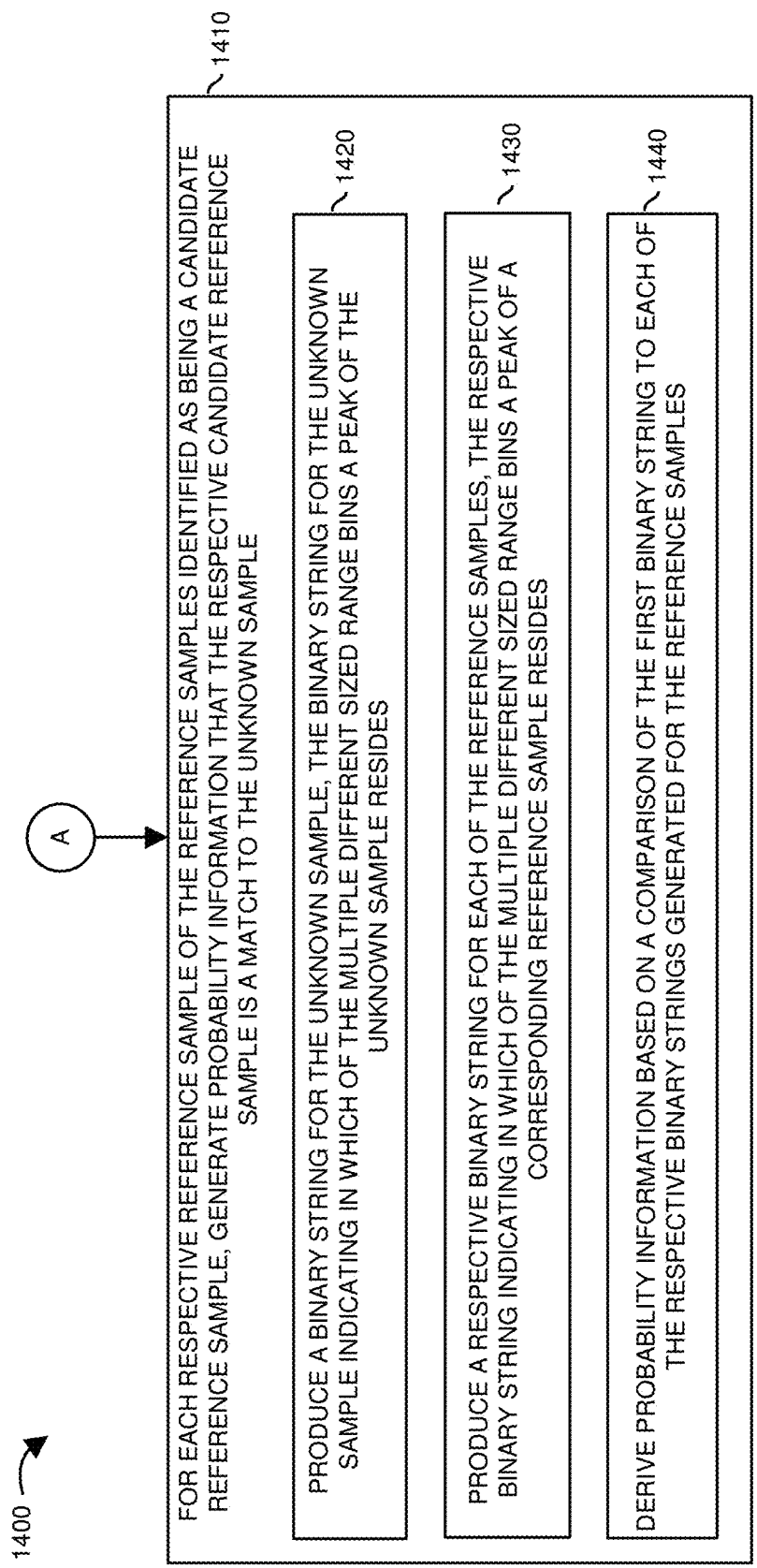

FIGS. 13 and 14 combine to form a flowchart 1300 (e.g., flowchart 1300-1 and flowchart 1300-2) illustrating an example method according to embodiments herein. Note that there will be some overlap with respect to concepts as discussed above.

In step 1310, a spectral data processor 120 receives a corresponding set of peaks for each reference sample of multiple references samples.

In step 1320, the spectral data processor 120 partitions a spectrum to include multiple different sized range bins 210. The spectral data processor 120 partitions the spectrum such that each of the peaks associated with the multiple reference samples resides in one of the multiple different sized range bins 210.

In sub-step 1325, the spectral data processor 120 defines widths of each of the multiple different sized range bins 210 such that a substantially equal number of the peaks in the reference samples fall into each of the multiple different sized range bins 210.

In step 1330, the application 140 indexes, maps, or compares locations of peaks associated with an unknown sample to locations of the multiple different sized range bins 210 in the divided spectrum.

In sub-step 1335, the application 140 indexes the peaks associated with the unknown sample into the multiple different sized range bins 210.

In sub-step 1340, based on the indexing, the application 140 identifies reference samples that are good candidate matches (e.g., possible matches) to the unknown sample under test.

In step 1410 of FIG. 14, for each respective reference sample of the reference samples identified as being a candidate reference sample, or alternatively any or all of the reference samples 105 in a pool, the analyzer application 140 generates probability information 170 indicating a degree to which each of the respective candidate reference samples matches the unknown sample.

In sub-step 1420, the analyzer application 140 produces a binary string 510 for the unknown sample. The binary string 510 for the unknown sample indicates in which of the multiple different sized range bins 210 one or more peaks of the unknown sample reside.

In sub-step 1430, the analyzer application 140 produces a respective binary string 610 for each of the reference samples. The respective binary string 610 indicates in which of the multiple different sized range bins at least one peak of a corresponding reference sample resides.

In sub-step 1440, the analyzer application 140 derives probability information 170 based on a comparison of the binary string 510 to each of one or more respective binary strings 610 generated for the reference samples.

Additional Embodiments and Claims

In a manner as discussed above, note that embodiments herein include generating and storing the peak and bin information 130. For example, as discussed above, spectral data processor 120 can be configured to receive spectral information 110 (e.g., indicating a set of peaks for each reference sample of multiple references samples). The spectral data processor 120 partitions a spectrum to include multiple different sized range bins 210. Each of the peaks (as specified by the spectral information 110) in the multiple reference samples resides in one of the multiple different sized range bins 210. The spectral data processor 120 stores peak information and bin information as peak and bin information 130. Stored peak and bin information 130 includes bin information indicating the multiple different sized range bins generated for the partitioned spectrum. Stored peak information of the peak and bin information 130 indicates in which of the multiple different sized range bins 210 the peaks in the multiple reference samples reside.

In a manner as discussed above, note that embodiments herein include identifying possible matches between an unknown sample and the multiple reference samples. For example, as discussed above, analyzer application 140 can be configured to access peak and bin information 130. More specifically, in one embodiment, the analyzer application 140 receives range bin information (e.g., peak and bin information 130). The range bin information indicates multiple different sized range bins 210 into which a spectrum has been partitioned. The analyzer application 140 further receives peak information from peak and bin information 130. The peak information indicates a set of peaks associated with each of the multiple reference samples. The peak information further indicates in which of the multiple different sized range bins 210 each of the peaks resides. To identify probable candidates that match the unknown sample, the analyzer application 140 indexes locations of peaks associated with an unknown sample to the multiple different sized range bins 210.

Note again that techniques herein are well suited for use in searching applications and matching of an unknown sample under test to one or more known reference samples. However, it should be noted that embodiments herein are not limited to use in such applications and that the techniques discussed herein are well suited for other applications as well.

As mentioned, embodiments herein are useful in applications where data compression is advantageous. By way of a non-limiting example, in systems configured with very little physical memory and/or processing resources, this process as discussed herein might just be used to produce compressed data that is then sent elsewhere for further analysis. More specifically, a remote device can be configured to store the range bin information generated for a pool of reference samples. The remote device can receive peak information for a sample under test and compare the locations of peaks associated with an unknown sample to generate a binary string indicating in which of the bins the unknown sample has a respective peak. The remote device can be configured to forward the generated binary string (e.g., compressed data) over a link to another location that performs further processing such as comparison of the binary string to binary strings associated with the reference samples to find one or more matches.

Based on the description set forth herein, numerous specific details have been set forth to provide a thorough understanding of claimed subject matter. However, it will be understood by those skilled in the art that claimed subject matter may be practiced without these specific details. In other instances, methods, apparatuses, systems, etc., that would be known by one of ordinary skill have not been described in detail so as not to obscure claimed subject matter. Some portions of the detailed description have been presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm as described herein, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has been convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing platform, such as a computer or a similar electronic computing device, that manipulates or transforms data represented as physical electronic or magnetic quantities within memories, registers, or other information storage devices, transmission devices, or display devices of the computing platform.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

We claim:

1. A method comprising:
   receiving spectral information for multiple reference samples using a spectral data processor, each reference sample associated with a different material and comprising a plurality of peak wavelengths distributed across a spectrum that identifies the material;
   producing peak and bin information that comprises the spectrum partitioned into multiple different sized range bins using a distribution of combined peak wavelengths compressed from the spectral information of the multiple reference samples across the spectrum, each range bin comprising a substantially equal number of the combined peak wavelengths and at least one peak wavelength from two or more of the reference samples, wherein the peak and bin information is produced by the spectral data processor and the peak and bin information also comprises a signature for each reference sample that includes an indication for each of the range bins that corresponds to the presence or absence of a peak wavelength for the reference sample;
   storing the peak and bin information for the reference samples on a handheld device comprising a memory and a processing resource that performs a method comprising:
      analyzing an unknown sample to produce spectral information from the unknown sample;
      indexing a plurality of peak wavelengths in the spectral information from the unknown sample to the range bins in the partitioned spectrum to produce a signature of the unknown sample that includes an indication for each of the range bins that corresponds to the presence or absence of a peak wavelength from the unknown sample;
      generating probability information that identifies the spectral information of a reference sample as a best match to the spectral information of the unknown sample by comparing the signature of the unknown sample to the signature of each reference sample; and
      notifying a user of the material associated with the reference sample that is a best match to the unknown sample to a user via a display screen on the handheld device.

2. The method as in claim 1, wherein the step of generating probability information includes:
   identifying a subset of the multiple reference samples with probability information that indicates candidate matches to the unknown sample.

3. The method as in claim 2, wherein the step of generating probability information includes:
   for each respective reference sample of the multiple reference samples:
      generating a value, k, indicating a number of occurrences that a peak wavelength of the unknown sample falls into a bin in which the respective reference also includes a peak wavelength;
      generating a value, N, indicating a number of the multiple different sized bins;
      generating a value, n, indicating a total number of peak wavelengths present in the respective reference sample; and
      generating a value, m, indicating a total number of peak wavelengths present in the unknown sample.

4. The method as in claim 3 further comprising:
generating the probability information for each of the respective reference samples using the following equation:

$$CDF(X = k) = f(k, N, m, n) = \sum_{i=0}^{k} \frac{\binom{m}{i}\binom{N-m}{n-i}}{\binom{N}{n}}.$$

5. The method as in claim 1, wherein the step of producing peak and bin information includes:
defining widths of each of the multiple different sized range bins such that a desired number of the combined peak wavelengths fall into each of the multiple different sized range bins.

6. The method as in claim 1 further comprising:
the probability information is generated using binary fixed-point arithmetic.

7. The method as in claim 1, wherein:
the spectral data processor processes the spectral information for the multiple reference samples to identify the plurality of peak wavelengths for each reference sample.

8. The method as in claim 1, wherein the step of producing peak and bin information includes:
selecting boundaries of the different sized range bins in accordance with a hypergeometric distribution model.

9. The method as in claim 1 further comprising:
implementing a hypergeometric probability function to generate the probability information.

10. The method as in claim 1 wherein the step of indexing includes:
identifying that a peak wavelength of the unknown sample resides within a particular range bin of the multiple range bins and assigning the indication in the signature for the unknown sample.

11. The method as in claim 1 wherein the step of generating includes:
computing the probability information to test a null hypothesis that peak wavelength matches between the reference sample and a given reference sample occurred by chance.

12. The method as in claim 1, wherein:
the signature of the unknown sample comprises a first binary string indicating in which of the multiple different sized range bins a peak wavelength of the unknown sample resides; and
generating the probability information that identifies the best match based on a similarity between the first binary string and the signature of a reference sample comprising a second binary string indicating in which of the multiple different sized range bins a peak wavelength of the reference sample resides.

13. A system comprising:
a spectral data processor;
a hardware storage resource coupled to the processor, the hardware storage resource storing instructions that, when executed by the spectral data processor, cause the spectral data processor to perform the operations of:
receiving spectral information for multiple reference samples each reference sample associated with a different material and comprising a plurality of peak wavelengths distributed across a spectrum that identifies the material;
producing peak and bin information that comprises the spectrum partitioned into multiple different sized range bins using a distribution of combined peak wavelengths compressed from the spectral information of the multiple reference samples across the spectrum, each range bin comprising a substantially equal number of the combined peak wavelengths and at least one peak wavelength from two or more of the reference samples, wherein the peak and bin information comprises a signature for each reference sample that includes an indication for each of the range bins that corresponds to the presence or absence of a peak wavelength for the reference sample; and
storing the peak and bin information for the reference samples in a memory resource of a handheld device;
the handheld device comprising a processing resource and the memory resource storing instructions that, when executed by the processing resource, cause the processing resource to perform the operations of:
analyzing an unknown sample to produce spectral information from the unknown sample;
indexing a plurality of peak wavelengths in the spectral information from the unknown sample to the range bins in the partitioned spectrum to produce a signature of the unknown sample that includes an indication for each of the range bins that corresponds to the presence or absence of a peak wavelength from the unknown sample;
generating probability information that identifies the spectral information of a reference sample as a best match to the spectral information of the unknown sample by comparing the signature of the unknown sample to the signature of each reference sample; and
notifying a user of the material associated with the reference sample that is a best match to the unknown sample to a user via a display screen on the handheld device.

14. The system as in claim 13, wherein the step of generating probability information includes:
identifying a subset of the multiple reference samples with probability information that indicates candidate matches to the unknown sample.

15. The system as in claim 13, wherein the step of producing peak and bin information includes:
defining widths of each of the multiple different sized range bins such that a desired number of the combined peak wavelengths fall into each of the multiple different sized range bins.

16. The system as in claim 13, in which the spectral data processor further performs operations of:
computing the probability information using binary fixed-point arithmetic.

17. A method comprising:
storing peak and bin information in a memory resource of a handheld device, wherein the peak and bin information comprises a spectrum partitioned into multiple different sized range bins using a distribution of combined peak wavelengths compressed from spectral information of multiple reference samples across the spectrum, each range bin comprising a substantially equal number of combined peak wavelengths and at least one peak wavelength from two or more of the reference samples, wherein each reference sample is associated with a different material and the spectral information comprises a plurality of peaks distributed across a spectrum that identifies the material, and wherein the peak and bin information comprises a signature for each reference sample that includes an indication for each of the range bins that corresponds to the presence or absence of a peak wavelength for the reference sample;

analyzing an unknown sample to produce spectral information from the unknown sample;

indexing a plurality of peak wavelengths in the spectral information from the unknown sample to the-range bins in the partitioned spectrum to produce a signature of the unknown sample that includes an indication for each of the range bins that corresponds the presence or absence of a peak wavelength from the unknown sample;

generating probability information that identifies the spectral information of a reference sample as a best match to the spectral information of the unknown sample by comparing the signature of the unknown sample to the signature of each reference sample; and notifying a user of the material associated with the reference sample that is a best match to the unknown sample to a user via a display screen on the handheld device.

18. The method as in claim 17 further comprising:
identifying a subset of the multiple reference samples with probability information that indicates candidate matches to the unknown sample.

19. The method as in claim 17, wherein widths of each of the multiple different sized range bins are defined such that a desired number of the combined peak wavelengths fall into each of the multiple different sized range bins.

20. The method as in claim 17 further comprising:
the probability information is generated using binary fixed-point arithmetic.

21. The method as in claim 17 further comprising:
implementing a hypergeometric probability function to generate the probability information.

22. A spectral analyzer comprising:
a handheld device comprising a display screen, a memory resource, and a processing resource, wherein:
the memory resource comprises peak and bin information stored thereon that comprises a spectrum partitioned into multiple different sized range bins using a distribution of combined peak wavelengths compressed from spectral information of multiple reference samples across the spectrum, each range bin comprising a substantially equal number of combined peak wavelengths and at least one peak wavelength from two or more of the reference samples, wherein each reference sample is associated with a different material and the spectral information comprises a plurality of peaks distributed across a spectrum that identifies the material, and wherein the peak and bin information comprises a signature for each reference sample that includes an indication for each of the range bins that corresponds to the presence or absence of a peak wavelength for the reference sample; and the processing resource performs a method comprising:
producing spectral information from an unknown sample;

indexing a plurality of peak wavelengths in the spectral information from the unknown sample to the range bins in the partitioned spectrum to produce a signature of the unknown sample that includes an indication for each of the range bins that corresponds the presence or absence of a peak wavelength from the unknown sample;

generating probability information that identifies the spectral information of a reference sample as a best match to the spectral information of the unknown sample by comparing the signature of the unknown sample to the signature of each reference sample; and notifying a user of the material associated with the reference sample that is a best match to the unknown sample to a user via the display screen on the handheld device.

23. The spectral analyzer as in claim 22 further comprising:
identifying a subset of the multiple reference samples with probability information that indicates candidate matches to the unknown sample.

24. The spectral analyzer as in claim 22, wherein widths of each of the multiple different sized range bins are defined such that a desired number of the combined peak wavelengths fall into each of the multiple different sized range bins.

25. The spectral analyzer as in claim 22 further comprising:
the probability information is generated using binary fixed-point arithmetic.

26. The spectral analyzer as in claim 22 further comprising:
implementing a hypergeometric probability function to generate the probability information.

* * * * *